United States Patent
Murakami et al.

(10) Patent No.: US 11,744,792 B2
(45) Date of Patent: Sep. 5, 2023

(54) SOLID SOAP

(71) Applicant: NOF CORPORATION, Tokyo (JP)

(72) Inventors: Dai Murakami, Amagasaki (JP); Tomohiro Wakita, Amagasaki (JP)

(73) Assignee: NOF CORPORATION, Tokyo (JP)

( * ) Notice: Subject to any disclaimer, the term of this patent is extended or adjusted under 35 U.S.C. 154(b) by 134 days.

(21) Appl. No.: 17/424,162

(22) PCT Filed: Jan. 16, 2020

(86) PCT No.: PCT/JP2020/001231
§ 371 (c)(1),
(2) Date: Jul. 20, 2021

(87) PCT Pub. No.: WO2020/153216
PCT Pub. Date: Jul. 30, 2020

(65) Prior Publication Data
US 2022/0110857 A1   Apr. 14, 2022

(30) Foreign Application Priority Data
Jan. 21, 2019   (JP) .................. 2019-007602

(51) Int. Cl.
*A61K 8/92* (2006.01)
*A61K 8/02* (2006.01)
*A61K 8/34* (2006.01)
*A61Q 19/10* (2006.01)

(52) U.S. Cl.
CPC .............. *A61K 8/92* (2013.01); *A61K 8/0216* (2013.01); *A61K 8/345* (2013.01); *A61Q 19/10* (2013.01); *A61K 2800/591* (2013.01)

(58) Field of Classification Search
CPC .............. A61K 8/361; A61K 2800/591; A61K 8/0216; A61K 8/19; A61K 8/345; A61K 47/60; A61K 9/127; A61K 2039/55566; A61K 8/14; A61K 31/795; A61K 39/0011; A61K 39/39; A61K 47/14; A61K 47/24; A61K 8/02; A61K 8/553; A61K 9/0095; A61K 9/107; A61K 9/1075; A61K 9/1271; A61K 9/1273; A61K 9/1278; A61K 8/8164; A61K 8/86; A61K 9/0014; A61K 9/0019; A61Q 19/10; C11D 9/007; C11D 9/02; C11D 17/0047; C11D 9/265; C11D 13/20; C11D 9/267; C11D 13/00; C11D 17/06; C11D 1/345; C11D 3/3707
See application file for complete search history.

(56) References Cited

FOREIGN PATENT DOCUMENTS

| JP | 10-503244 A | * | 3/1998 | ............... C11D 9/26 |
|---|---|---|---|---|
| JP | H10503234 A | | 3/1998 | |
| JP | 2000-160196 A | * | 6/2000 | ............... C11D 9/02 |
| JP | 2000160196 A | | 6/2000 | |
| JP | 201679350 A | | 5/2016 | |

OTHER PUBLICATIONS

JP10-503244A translation, provided by Applicant in IDS dated Jul. 19, 2021 (Year: 1998).*
JP2000-160196A translation, provided by Applicant in IDS dated Jul. 19, 2021 (Year: 2000).*
International Search Report of PCT Patent Application No. PCT/JP2020/001231 dated Mar. 24, 2020.

* cited by examiner

*Primary Examiner* — Audrea B Coniglio

(57) ABSTRACT

A solid soap containing, (A) 77 to 91 mass % of an alkali metal salt of a saturated fatty acid having an even number of carbon atoms from 12 to 18, (B) 0.005 to 1 mass % of an alkali metal salt of a saturated fatty acid having an odd number of carbon atoms from 13 to 17, (C) 0.5 to 5 mass % of glycerol, and (D) 5 to 18 mass % of water.

2 Claims, No Drawings

SOLID SOAP

BACKGROUND OF THE INVENTION

1. Field of the Invention

The present invention relates to solid soaps used for cleaning the skin.

2. Description of the Related Art

Conventionally, soaps, which are fatty acid salts, are commonly used as cleansing agents for the skin of faces, bodies, and the like. Soaps are bases that not only provide a unique refreshing feeling after washing but also have good biodegradability and are environmentally friendly. Among these soaps, solid soap is widely used as a general cleansing agent for the skin. For example, as the fatty acids included in the solid soap, mixed fatty acids produced from oils and fats such as coconut oil, palm oil, and palm kernel oil are used, and these mixed fatty acids contain about 30 to 40 mass % of unsaturated fatty acids. Although unsaturated fatty acids are effective in maintaining the solubility and formability of soap, there is a problem in that unsaturated fatty acids have low storage stability and are prone to discoloration and odor deterioration.

In order to improve the storage stability of solid soaps, a solid soap obtained by using only saturated fatty acids has been proposed. Using only saturated fatty acids improves solid soaps in terms of discoloration and odor deterioration. However, there are problems in that cracks are generated in the solid soap during stamping, which leads to reduced productivity, and the solubility of the solid soap during use decreases. In order to solve these problems, PTL 1 proposes, for example, a solid soap containing a fatty acid and an alkali metal salt of a saturated fatty acid having an even number of carbon atoms.

Further, solid soaps obtained by using only saturated fatty acids may not foam well in cold water. In order to solve this problem, PTL 2 proposes a framed solid soap containing a salt of a saturated fatty acid having an even number of carbon atoms, a dihydric alcohol, a polymer having 2-methacryloyloxyethyl phosphorylcholine and (meth)acrylic acid alkyl ester as constituent monomers, and a cationic polymer.

In addition, when shaving downy hair of the face and body with a shaver, solid soap may be used for the purpose of imparting slipperiness, and in order to further improve the slipperiness, it is preferable to apply the soap in a high concentration to the face or the body. However, when the soap concentration is high, the soap does not spread well and it is difficult to apply the soap over a wide area. Therefore, there is a demand for a solid soap that spreads well when being used in a high concentration, and capable of imparting excellent slipperiness.

CITATION LIST

Patent Literature

[PTL 1] Japanese Unexamined Patent Application Publication No. 2000-160196 A
[PTL 2] Japanese Unexamined Patent Application Publication No. 2016-79350 A

SUMMARY OF THE INVENTION

Technical Problem

The present invention relates to a solid soap and an object of the present invention is to provide a solid soap that is produced with excellent productivity, easily foams not only in lukewarm water, but also in cold water, and has good spreadability and slipperiness on the skin.

Solution to Problem

As a result of diligent studies to solve the above problems, the present inventors have found that a solid soap having the desired effect can be obtained by selecting specific materials and setting the blending ratio thereof within a specific range, which led to the completion of the present invention.

That is, the present invention is a solid soap containing,
(A) 77 to 91 mass % of an alkali metal salt of a saturated fatty acid having an even number of carbon atoms from 12 to 18,
(B) 0.005 to 1 mass % of an alkali metal salt of a saturated fatty acid having an odd number of carbon atoms from 13 to 17,
(C) 0.5 to 5 mass % of glycerol, and
(D) 5 to 18 mass % of water.

Advantageous Effects of Invention

The solid soap according to the present invention is produced with excellent productivity, because adhesion of the soap to a die during production and generation of cracks on a surface of the soap after forming are suppressed. Further, the solid soap according to the present invention foams well not only in lukewarm water but also in cold water. Moreover, the solid soap according to the present invention spreads well when being used in a high concentration, and is capable of imparting excellent slipperiness.

DETAILED DESCRIPTION OF THE PREFERRED EMBODIMENTS

Embodiments of the present invention will be described below. The solid soap according to the present invention contains component (A), component (B), component (C), and component (D) mentioned below. The components are described below.

Note that numerical ranges specified herein using the word "to" include numerical values on both sides of the word "to" (an upper limit and a lower limit). For example, "2 to 10" means a range of 2 or more and 10 or less.

Further, when a concentration or an amount is specified, any higher concentration or amount can be associated with any lower concentration or amount. For example, when ranges of "2 to 10 mass %" and "preferably 4 to 8 mass %" are mentioned, this expression also includes ranges such as "2 to 4 mass %", "2 to 8 mass %", "4 to 10 mass %", and "8 to 10 mass %".

Component (A): Alkali Metal Salt of Even-Chain Saturated Fatty Acid

Component (A) used in the present invention is an alkali metal salt of a saturated fatty acid having an even number of carbon atoms from 12 to 18 (also referred to as an "even-chain saturated fatty acid" herein), in other words, an alkali metal salt of a saturated fatty acid having 12, 14, 16, or 18 carbon atoms.

Examples of the even-chain saturated fatty acid used as component (A) include lauric acid, myristic acid, palmitic acid, and stearic acid, and it is preferable to combine lauric acid, myristic acid, and palmitic acid. The total content of these three fatty acids in component (A) is preferably 95 to 100 mass %, and more preferably 97 to 100 mass %. The mass ratio in the range mentioned above is more preferable from the viewpoint of productivity and foamability in cold water.

The alkali metals used for component (A) are potassium and sodium, and it is preferable to combine potassium and sodium. Further, in order to obtain an alkali metal salt of an even-chain saturated fatty acid, it is preferable to use a combination of potassium hydroxide and sodium hydroxide to neutralize even-chain fatty acids. In this case, the mass ratio of potassium hydroxide/sodium hydroxide is preferably 1/4 to 3/2, more preferably 1/3 to 1/1, and particularly preferably 2/5 to 4/5. The mass ratio in the range mentioned above is more preferable from the viewpoint of productivity and foamability in cold water.

The content of component (A) is 77 to 91 mass %, preferably 78 to 90 mass %, and more preferably 80 to 88 mass %, with respect to the total amount of the solid soap. If the content of component (A) is too low, the productivity and the foamability may decrease. On the other hand, if the content of component (A) is too large, the productivity, the foamability in cold water, the spreadability, and the slipperiness may decrease.

Component (B): Alkali Metal Salt of Odd-Chain Saturated Fatty Acid

Component (B) used in the present invention is an alkali metal salt of a saturated fatty acid having an odd number of carbon atoms from 13 to 17 (also referred to as an "odd-chain saturated fatty acid" herein), in other words, an alkali metal salt of a saturated fatty acid having 13, 15, or 17 carbon atoms.

Examples of the odd-chain saturated fatty acid used in component (B) include tridecanoic acid, pentadecanoic acid, and heptadecanoic acid, and pentadecanoic acid and heptadecanoic acid are preferable, and it is more preferable to use pentadecanoic acid and heptadecanoic acid in combination.

When pentadecanoic acid and heptadecanoic acid are used in combination, the mass ratio of pentadecanoic acid/heptadecanoic acid is preferably 1/30 to 30/1, more preferably 1/10 to 10/1, still more preferably 1/5 to 5/1, and particularly preferably 1/3 to 3/1. The mass ratio in the range mentioned above is more preferable from the viewpoint of spreadability and slipperiness.

Further, the total content of pentadecanoic acid and heptadecanoic acid in component (B) is preferably 95 to 100 mass %, and more preferably 97 to 100 mass %. When the content of pentadecanoic acid and heptadecanoic acid is in the range mentioned above, spreadability and slipperiness can be well-balanced.

The alkali metals used for component (B) are potassium and sodium, and it is preferable to combine potassium and sodium. Further, in order to obtain an alkali metal salt of an odd-chain saturated fatty acid, it is preferable to use a combination of potassium hydroxide and sodium hydroxide to neutralize odd-chain fatty acids. In this case, the mass ratio of potassium hydroxide/sodium hydroxide is preferably 1/4 to 3/2, more preferably 1/3 to 1/1, and particularly preferably 2/5 to 4/5. The mass ratio in the range mentioned above is more preferable from the viewpoint of productivity and foamability in cold water.

The content of component (B) is 0.005 to 1 mass %, preferably 0.01 to 0.7 mass %, more preferably 0.03 to 0.5 mass %, and particularly preferably 0.05 to 0.3 mass %, with respect to the total amount of the solid soap. If the content of component (B) is too low, the productivity, the foamability in cold water, the spreadability, and the slipperiness may decrease. On the other hand, if the content of component (B) is too large, an effect corresponding to a blending amount may not be achieved, which may be economically disadvantageous, and in some cases, the productivity, the spreadability, and the slipperiness may decrease.

Component (C): Glycerol

Component (C) used in the present invention is glycerol. Glycerol can be produced by a method in which an aqueous solution obtained by hydrolysis of oils and fats is purified by distillation or the like.

The content of component (C) is 0.5 to 5 mass %, preferably 1 to 4 mass %, and more preferably 1.5 to 3.5 mass %, with respect to the total amount of the solid soap. If the content of component (C) is too low, the foamability in cold water, the spreadability, and the slipperiness may decrease. On the other hand, if the content of component (C) is too large, the productivity may decrease.

Component (D): Water

Component (D) used in the present invention is water.

Component (D) is preferably deionized water, ion-exchanged water, or distilled water.

The content of component (D) is 5 to 18 mass %, preferably 6 to 16 mass %, and more preferably 7 to 14 mass %, with respect to the total amount of the solid soap. If the content of component (D) is too low, the productivity and the foamability in cold water may decrease. On the other hand, if the content of component (D) is too large, the productivity may decrease.

In the solid soap according to the present invention, the total content of components (A) to (D) is 82.55 to 100 mass %, preferably 85 to 100 mass %, more preferably 90 to 100 mass %, and particularly preferably 95 to 100 mass %, with respect to the total amount of the solid soap.

Other Components

In addition to components (A) to (D), the solid soap according to the present invention may contain components commonly used for solid soaps as other components.

Examples of the other components include oils and fats such as vegetable oils and fats, animal oils and fats; fatty acids; pH adjusting agents; antioxidants; metal sequestering agents; dyes; fragrances; and pigments. When the solid soap according to the present invention contains another component, the content of the other component is preferably 17 mass % or less, and more preferably 10 mass % or less, with respect to the total amount of the solid soap.

From the viewpoint of improving the foam quality, it is preferable that a saturated fatty acid is contained as the other component, and it is preferable to select one or more from lauric acid, myristic acid, and palmitic acid as the saturated fatty acid. When the solid soap according to the present invention contains a fatty acid, the content of the fatty acid is preferably 0.1 to 10 mass %, more preferably 0.5 to 8 mass %, and particularly preferably 1 to 5 mass %.

The solid soap according to the present invention can be produced by applying a common method such as framing or milling to a mixture of the components mentioned above.

EXAMPLES

Below, the present invention will be described in more detail with reference to examples and comparative examples. The compositions and components shown in Tables 1 to 4 below were used to prepare a solid soap by the method described in the following production example.

Production Example

A fatty acid (a mixed fatty acid of component (A) and component (B)) was put into a 5 L double-arm kneading machine (manufactured by Irie Shokai Co., Ltd., PNV-5 type) and melted at about 80° C.

Subsequently, a mixture of a 28 mass % sodium hydroxide aqueous solution and a 28 mass % potassium hydroxide aqueous solution was added, and the mixture was stirred and mixed at 85 to 95° C. for about 5 minutes. Next, glycerol was added, and the mixture was further stirred and mixed at the same temperature to dry the mixture and adjust its water content. The composition was kneaded three times with a plodder (manufactured by Nippon Kakoki Co., Ltd., Mini Soap Plodder) and a roll mill (manufactured by Imex Co., Ltd., BR-150 type bench roll), to obtain a soap bar in the plodder. Subsequently, the composition was formed in a stamping machine (FP-171 manufactured by Nippon Kakoki Co., Ltd.) to obtain a solid soap.

The following raw materials were used.

Lauric acid: Special grade reagent (manufactured by Tokyo Chemical Industry Co., Ltd.)
Myristic acid: Special grade reagent (manufactured by Tokyo Chemical Industry Co., Ltd.)
Palmitic acid: Special grade reagent (manufactured by Tokyo Chemical Industry Co., Ltd.)
Stearic acid: Special grade reagent (manufactured by Tokyo Chemical Industry Co., Ltd.)
Pentadecanoic acid: Special grade reagent (manufactured by Tokyo Chemical Industry Co., Ltd.)
Heptadecanoic acid: Special grade reagent (manufactured by Tokyo Chemical Industry Co., Ltd.)
Glycerol: Special grade reagent (manufactured by Tokyo Chemical Industry Co., Ltd.)

Component (A)

Mixtures of potassium hydroxide/sodium hydroxide in the mass ratios shown in Table 1 were added to mixed fatty acids mixed according to the blending ratios shown in Table 1 below, and the mixtures were stirred and mixed to prepare fatty acid salts (A1) to (A4) to be used as component (A).

TABLE 1

|  | Fatty acid composition (mass %) | | | |
| --- | --- | --- | --- | --- |
|  | A1 | A2 | A3 | A4 |
| Lauric acid (C12) | 30 | 30 | 30 | 30 |
| Myristic acid (C14) | 60 | 60 | 60 | 60 |
| Palmitic acid (C16) | 10 | 7 | 10 | 10 |
| Stearic acid (C18) | — | 3 | — | — |
| Potassium hydroxide/sodium hydroxide | 2/3 | 2/3 | 1/3 | 1/1 |

Component (B)

Mixtures of potassium hydroxide/sodium hydroxide in the mass ratios shown in Table 2 were added to mixed fatty acids mixed according to the blending ratios shown in Table 2 below, and the mixtures were stirred and mixed to prepare fatty acid salts (B1) to (B5) to be used as component (B).

TABLE 2

|  | Fatty acid composition (mass %) | | | | |
| --- | --- | --- | --- | --- | --- |
|  | B1 | B2 | B3 | B4 | B5 |
| Pentadecanoic acid (C15) | 100 | — | 50 | 50 | 50 |
| Heptadecanoic acid (C17) | — | 100 | 50 | 50 | 50 |
| Potassium hydroxide/sodium hydroxide | 2/3 | 2/3 | 2/3 | 1/3 | 1/1 |

Examples 1 to 10 and Comparative Examples 1 and 2

Solid soaps were prepared in the above-described production example according to the blending ratios shown in Tables 3 and 4, and evaluated by the following method. The results are shown in Tables 3 and 4. Note that, "excellent" and "good" were determined to be acceptable.

<Evaluation Method>

(1) Foamability in Lukewarm Water (38° C.)

As panelists, 20 women aged from 25 to 55 participated. They wet their hands and the solid soap with lukewarm water at about 38° C. and rubbed the solid soap 10 times with their hands. Subsequently, foam was generated while gradually adding lukewarm water at about 38° C. The foam thus obtained was evaluated according to the following criteria.

2 points: The panelist felt very good foamability.
1 point: The panelist felt rather good foamability.
0 points: The panelist felt bad foamability.

The total scores of the 20 panelists were calculated and evaluated as follows.

Excellent: Total score from 36 to 40 points
Good: Total score from 31 to 35 points
Fair: Total score from 21 to 30 points
Poor: Total score of 20 points or less (2) Foamability in Cold Water (10° C.)

As panelists, 20 women aged from 25 to 55 participated. They wet their hands and the solid soap with cold water at about 10° C. and rubbed the solid soap 10 times with their hands. Subsequently, foam was generated while gradually adding cold water at about 10° C. The foam thus obtained was evaluated according to the following criteria.

2 points: The panelist felt very good foamability.
1 point: The panelist felt rather good foamability.
0 points: The panelist felt bad foamability.

The total of scores of the 20 panelists was calculated and evaluated as follows.

Excellent: Total score from 36 to 40 points
Good: Total score from 31 to 35 points
Fair: Total score from 21 to 30 points
Poor: Total score of 20 points or less (3) Spreadability and Slipperiness on Skin As panelists, 20 women aged from 25 to 55 participated. They wet their hands and the solid soap with lukewarm water at about 38° C. and rubbed the solid soap 10 times with their hands. Subsequently, the panelists applied the soap to their faces and bodies by hand to evaluate the spreadability and slipperiness according to the following criteria.

2 points: The panelist felt very good spreadability and slipperiness.
1 point: The panelist felt rather good spreadability and slipperiness.
0 points: The panelist felt bad spreadability and slipperiness.

The total scores of the 20 panelists were calculated and evaluated as follows.

Excellent: Total score from 36 to 40 points
Good: Total score from 31 to 35 points
Fair: Total score from 21 to 30 points
Poor: Total score of 20 points or less (4) Productivity An extruding machine and a stamping machine were used to form 20 solid soaps from the composition mixed in the kneading machine. Subsequently, the die was visually observed to check whether material adhered to the die exists, and further, the appearance of each soap after forming was visually observed to evaluate the soaps according to the following criteria.

Acceptable product: There is no material adhered to the die, and no cracks are visible on the surface of the soap after forming.

Unacceptable product: There is material adhered to the die, or cracks are visible on the surface of the soap after forming.

Excellent: The number of acceptable products is 19 or more.

Good: The number of acceptable products is from 15 to 18.

Fair: The number of acceptable products is from 11 to 14.

Poor: The number of acceptable products is 10 or less.

In Comparative Example 1, component (B) was not added, and thus, the foamability in cold water was poor, and the spreadability and slipperiness on the skin were insufficient.

In Comparative Example 2, the content of component (B) was high, and thus, the productivity was poor, and the spreadability and slipperiness on the skin were insufficient.

Example 11

A solid soap was prepared according to the formulation described below and evaluated in the same manner as in the examples described above.

TABLE 3

| | | Example (mass %) | | | | | | | | | |
|---|---|---|---|---|---|---|---|---|---|---|---|
| | | 1 | 2 | 3 | 4 | 5 | 6 | 7 | 8 | 9 | 10 |
| (A) | A1 | 78 | 90 | 88 | 88 | 85 | 85 | 85 | — | — | — |
| | A2 | — | — | — | — | — | — | — | 85 | — | — |
| | A3 | — | — | — | — | — | — | — | — | 85 | — |
| | A4 | — | — | — | — | — | — | — | — | — | 85 |
| (B) | B1 | 0.1 | 0.1 | — | — | — | — | — | — | — | — |
| | B2 | — | — | 0.005 | 0.5 | 0.1 | 0.1 | — | — | — | — |
| | B3 | — | — | — | — | — | — | 0.1 | 0.1 | — | — |
| | B4 | — | — | — | — | — | — | — | — | 0.1 | — |
| | B5 | — | — | — | — | — | — | — | — | — | 0.1 |
| (C) | Glycerol | 4 | 4 | 1 | 1 | 0.5 | 3 | 3 | 3 | 3 | 3 |
| (D) | Water | 17.9 | 5.9 | 10.995 | 10.5 | 14.4 | 11.9 | 11.9 | 11.9 | 11.9 | 11.9 |
| Total | | 100 | 100 | 100 | 100 | 100 | 100 | 100 | 100 | 100 | 100 |
| Evaluation item | Foamability in lukewarm water | Good (34) | Excellent (36) | Excellent (36) | Excellent (38) | Excellent (37) | Excellent (39) | Excellent (40) | Good (35) | Excellent (36) | Excellent (39) |
| | Foamability in cold water | Good (31) | Good (32) | Good (31) | Excellent (36) | Good (33) | Excellent (36) | Excellent (38) | Good (32) | Good (32) | Excellent (37) |
| | Spreading and slipperiness on skin | Good (34) | Good (31) | Good (31) | Good (35) | Good (32) | Good (33) | Excellent (37) | Good (33) | Excellent (36) | Excellent (36) |
| | Productivity | Good (15) | Good (16) | Good (18) | Excellent (19) | Excellent (20) | Excellent (20) | Excellent (20) | Good (18) | Good (17) | Good (18) |

TABLE 4

| | | Comparative Example (mass %) | |
|---|---|---|---|
| | | 1 | 2 |
| (A) | A1 | 88 | 88 |
| (B) | B2 | — | 6 |
| (C) | Glycerol | 1 | 1 |
| (D) | Water | 11 | 5 |
| Total | | 100 | 100 |
| Evaluation item | Foamability in lukewarm water | Good (33) | Good (34) |
| | Foamability in cold water | Fair (24) | Good (32) |
| | Spreading and slipperiness on skin | Fair (25) | Fair (29) |
| | Productivity | Good (16) | Fair (14) |

All of the solid soaps of Examples 1 to 10 were produced with excellent productivity, easily foamed not only in lukewarm water, but also in cold water, and had good spreadability and slipperiness on the skin.

In Comparative Examples 1 and 2, on the other hand, adequate performance is not obtained.

| (A) A3 | 85 mass % |
|---|---|
| (B) B3 | 0.05 mass % |
| (C) Glycerol | 1 mass % |
| (D) Water | 10 mass % |

(Other Components)

| Lauric acid | 3 mass % |
|---|---|
| Citric acid | 0.5 mass % |
| Tocopherol | 0.05 mass % |
| Tetrasodium etidronate | 0.2 mass % |
| Fragrance | 0.2 mass % |
| Total blending amount | 100 mass % |

The solid soap of Example 11 was produced with excellent productivity, easily foamed not only in lukewarm water, but also in cold water, and had good spreadability and slipperiness on the skin.

Example 12

A solid soap was prepared according to the formulation described below and evaluated in the same manner as in the examples described above.

| | | |
|---|---|---|
| (A) A1 | 81 | mass % |
| (B) B3 | 1 | mass % |
| (C) Glycerol | 5 | mass % |
| (D) Water | 8 | mass % |

(Other Components)

| | | |
|---|---|---|
| Lauric acid | 3 | mass % |
| Sodium methyl cocoyl taurate | 0.8 | mass % |
| Citric acid | 0.1 | mass % |
| Tocopherol | 0.1 | mass % |
| Tetrasodium etidronate | 0.1 | mass % |
| Tetrasodium edetate | 0.1 | mass % |
| Titanium oxide | 0.1 | mass % |
| PEG-9M | 0.1 | mass % |
| PEG-65M | 0.1 | mass % |
| Polyquaternium-7 | 0.1 | mass % |
| Polyquaternium-10 | 0.1 | mass % |
| Polyquaternium-51 | 0.1 | mass % |
| Polyquaternium-64 | 0.1 | mass % |
| Fragrance | 0.1 | mass % |
| Total blending amount | 100 | mass % |

The solid soap of Example 12 was produced with excellent productivity, easily foamed not only in lukewarm water, but also in cold water, and had good spreadability and slipperiness on the skin.

RELATED APPLICATIONS

The present application claims priority based on the Japanese Patent Application filed on Jan. 21, 2019 (Japanese Patent Application No. 2019-007602), the entire contents of which are incorporated herein by reference.

What is claimed is:

1. A solid soap, comprising:
   (A) 77 to 91 mass % of an alkali metal salt of a saturated fatty acid having an even number of carbon atoms from 12 to 18;
   (B) 0.005 to 1 mass % of an alkali metal salt of a saturated fatty acid having an odd number of carbon atoms from 13 to 17;
   (C) 0.5 to 5 mass % of glycerol; and
   (D) 5 to 14 mass % of water.

2. The solid soap according to claim 1, further comprising 0.1 to 10 mass % of a saturated fatty acid.

* * * * *